(12) United States Patent
Pettit et al.

(10) Patent No.: US 6,698,889 B2
(45) Date of Patent: *Mar. 2, 2004

(54) ADAPTIVE WAVEFRONT MODULATION SYSTEM AND METHOD FOR REFRACTIVE LASER SURGERY

(75) Inventors: George H. Pettit, Maitland, FL (US); John Alfred Campin, Orlando, FL (US)

(73) Assignee: Alcon, Inc., Hunenberg (CH)

(*) Notice: Subject to any disclaimer, the term of this patent is extended or adjusted under 35 U.S.C. 154(b) by 79 days.

This patent is subject to a terminal disclaimer.

(21) Appl. No.: 10/151,404

(22) Filed: May 20, 2002

(65) Prior Publication Data

US 2003/0133074 A1 Jul. 17, 2003

Related U.S. Application Data

(60) Provisional application No. 60/348,812, filed on Jan. 14, 2002.

(51) Int. Cl.[7] .................. A61B 3/00; A61B 19/00; G06F 17/30; G06F 7/00; G06F 17/60
(52) U.S. Cl. .................. 351/246; 351/200; 128/898; 707/3; 705/2; 705/3
(58) Field of Search .................. 351/200, 205–221, 351/246, 247; 128/898; 707/3; 705/2, 3; 607/88, 89; 604/289; 606/5

(56) References Cited

U.S. PATENT DOCUMENTS

| | | | |
|---|---|---|---|
| 4,669,466 A | 6/1987 | L'Esperance | |
| 4,721,379 A | 1/1988 | L'Esperance | |
| 5,106,183 A | 4/1992 | Yoder, Jr. | |
| 5,581,347 A | 12/1996 | Le Saux et al. | |
| 5,666,492 A | * 9/1997 | Rhodes et al. | 705/3 |
| 5,722,427 A | 3/1998 | Wakil et al. | |
| 5,735,283 A | 4/1998 | Snook | |
| 6,155,684 A | 12/2000 | Bille et al. | |
| 6,177,940 B1 | * 1/2001 | Bond et al. | 705/3 |
| 6,270,221 B1 | 8/2001 | Liang et al. | |
| 6,582,078 B2 | * 6/2003 | Halpern et al. | 351/205 |
| 6,618,721 B1 | * 9/2003 | Lee | 707/3 |
| 2003/0149597 A1 | * 8/2003 | Zaleski | 705/2 |

\* cited by examiner

*Primary Examiner*—Dennis W. Ruhl
*Assistant Examiner*—John R. Sanders
(74) *Attorney, Agent, or Firm*—Allen, Dyer, Doppelt, Milbrath & Gilchrist, P.A.

(57) ABSTRACT

A method for optimizing a prescription for laser-ablation corneal treatment includes the steps of receiving a measured correction prescription for a current patient having a classification element associated therewith, the prescription having been measured using wavefront determination. A database of treatment outcomes on a plurality of previously treated patients is accessed, each treated patient outcome having associated therewith at least one classification element and comprising a preoperative wavefront-determined correction prescription and a postoperative visual profile. From the treatment outcomes in the database is calculated an average difference between the preoperative prescription and the postoperative profile for at least some of the previously treated patients having a classification element in common with the current patient. Finally the current patient correction prescription is adjusted commensurate with the calculated average difference to form an optimized prescription.

22 Claims, 5 Drawing Sheets

ADAPTIVE WAVEFRONT MODULATION SYSTEM AND METHOD FOR REFRACTIVE LASER SURGERY

CROSS-REFERENCE TO RELATED APPLICATION

This application claims priority from commonly owned provisional application Ser. No. 60/348,812, filed Jan. 14, 2002, "Wavefront-Based Treatment Nomogram."

BACKGROUND OF THE INVENTION

1. Field of the Invention

The present invention relates to systems and methods for performing refractive laser surgery on the eye, and, more particularly, to such systems and methods that adaptively modulate sensed data on the basis of data from prior procedures.

2. Description of Related Art

In conventional refractive laser surgery a clinician typically modifies a prescription entered into the treatment system. Such modifications are based upon prior experience with outcomes achieved with that particular treatment system, and also upon experience with particular patient populations derived from, for example, demographic data. For example, a surgeon might enter a 2-diopter myopic treatment prescription for a patient diagnosed with 3 diopters of myopia if analysis of previous outcomes indicates a 50% overcorrection using this system for patients of a particular category. Such an empirical alteration of entered treatment parameters based upon previous experience is referred to as a nomogram adjustment. Nomograms are considered essential by the ophthalmic community because different clinicians employ different surgical techniques, operate under different environmental conditions, have distinct patient demographics, etc.

Conventional surgery involves a limited number of well-defined treatment parameters, principally spherical error, astigmatic error, astigmatic axis, optical zone size, and blend zone size. Thus it is relatively straightforward for a surgeon to develop nomogram formulas based on conventional clinical examinations before and after surgical procedures. In contrast, wavefront-guided customized treatments, such as that disclosed in commonly owned U.S. Pat. No. 6,270,221 B1, the disclosure of which is incorporated herein by reference, involve complex a mathematical description of the pre-operative aberration profile, which is transferred electronically to the treatment system.

Although such a precise wavefront description can in theory be modified empirically to yield a better outcome, typically clinicians are not skilled in the analytic interpretations of these mathematical parameters. In addition, at present there is no known convenient method for a surgeon to modify a wavefront-based prescription prior to a procedure such as laser surgery.

In currently used wavefront-based treatments, the raw wavefront data are modulated to generate a treatment profile in order to account for an apparent radial dependence in the effectiveness of ablative treatment on the corneal tissue. This, however, is currently applied identically in all treatments.

SUMMARY OF THE INVENTION

It is therefore an object of the present invention to provide a system and method for creating a nomogram for adaptively modulating sensed wavefront data based upon prior treatment outcomes.

It is a further object to provide such a system and method that are site-specific.

It is another object to provide such a system and method that are demographically based.

These and other objects are achieved by the present invention, one aspect of which is a method for refining a prescription for laser-ablation corneal treatment. The method comprises the steps of receiving a measured correction prescription for a current patient. Typically the prescription will have been obtained using a wavefront determination. The current patient will have associated with him/her a classification element for placing the patient in at least one particular category.

Next a database of treatment outcomes on a plurality of previously treated patients is accessed. The database contains, for each previously treated patient, at least one classification element and also comprises a preoperative wavefront-determined correction prescription and a postoperative visual profile. A difference between the preoperative correction prescription and the postoperative visual profile represents an over- or undercorrection resulting from the surgery.

Treatment outcome data are accessed from the database based upon possessing a classification element in common with the current patient. From these data, an average difference may be calculated between the preoperative prescription and the postoperative profile. This average difference is then used to adjust the current patient's correction prescription to form an optimized prescription prior to performing the procedure.

Another aspect of the present invention includes a software package for performing the calculational steps outlined above.

A further aspect includes a method for creating a system for optimizing a prescription for laser ablation surgery, which includes the steps of forming a database of treatment outcomes as described above. A search engine resident on a processor is adapted to extract treatment outcomes based upon a classification element. Software is also provided for performing the calculational steps as outlined above.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
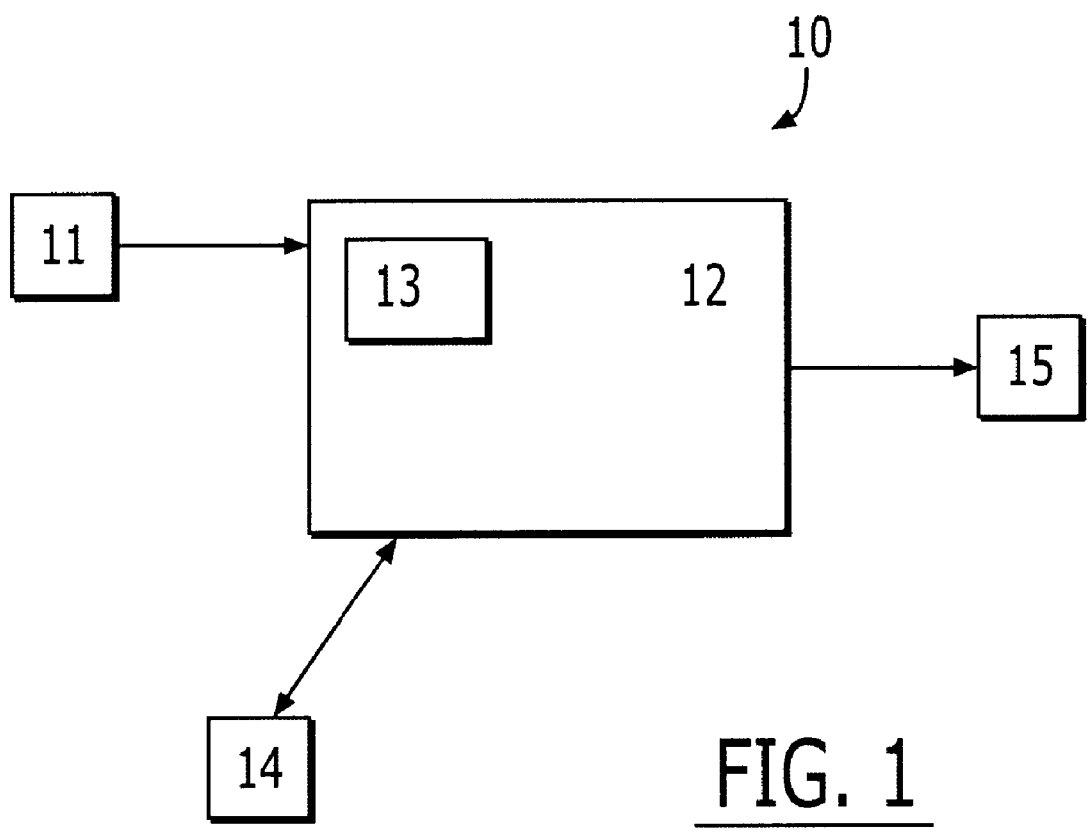
FIG. 1 is a schematic diagram of the system of the present invention.

A description of the preferred embodiments of the present invention will now be presented with reference to FIGS. 1–4.

The system 10 (FIG. 1) and method 100 (FIGS. 2A, 2B) of the present invention are directed, in a first embodiment, to an optimization of a prescription for laser-ablation corneal treatment. In a preferred embodiment a measured correction prescription will have been measured (block 101) using a wavefront determination apparatus 11 for a current patient. Typically the correction prescription comprises an algorithm having a plurality of terms, each of which has associated therewith a coefficient. For example, the wavefront may be described mathematically using a standardized form, such as Zernike polynomials, Taylor polynomials, or Fourier series, although these are not intended as limitations. For any such form describing a mathematical shape, a specific wavefront can be described by the numerical values for the weighting of the various terms in the mathematical expression.

The raw correction prescription is received into a processor 12 housing a software package 13 for a current patient (block 102) having a uniquely associated classification element. Among the classification elements may be included such data as, but not intended to be limited to, patient-specific data, such as age, gender, and ethnic background, and site-specific data such as local elevation and environmental parameters such as humidity.

Figure 4:
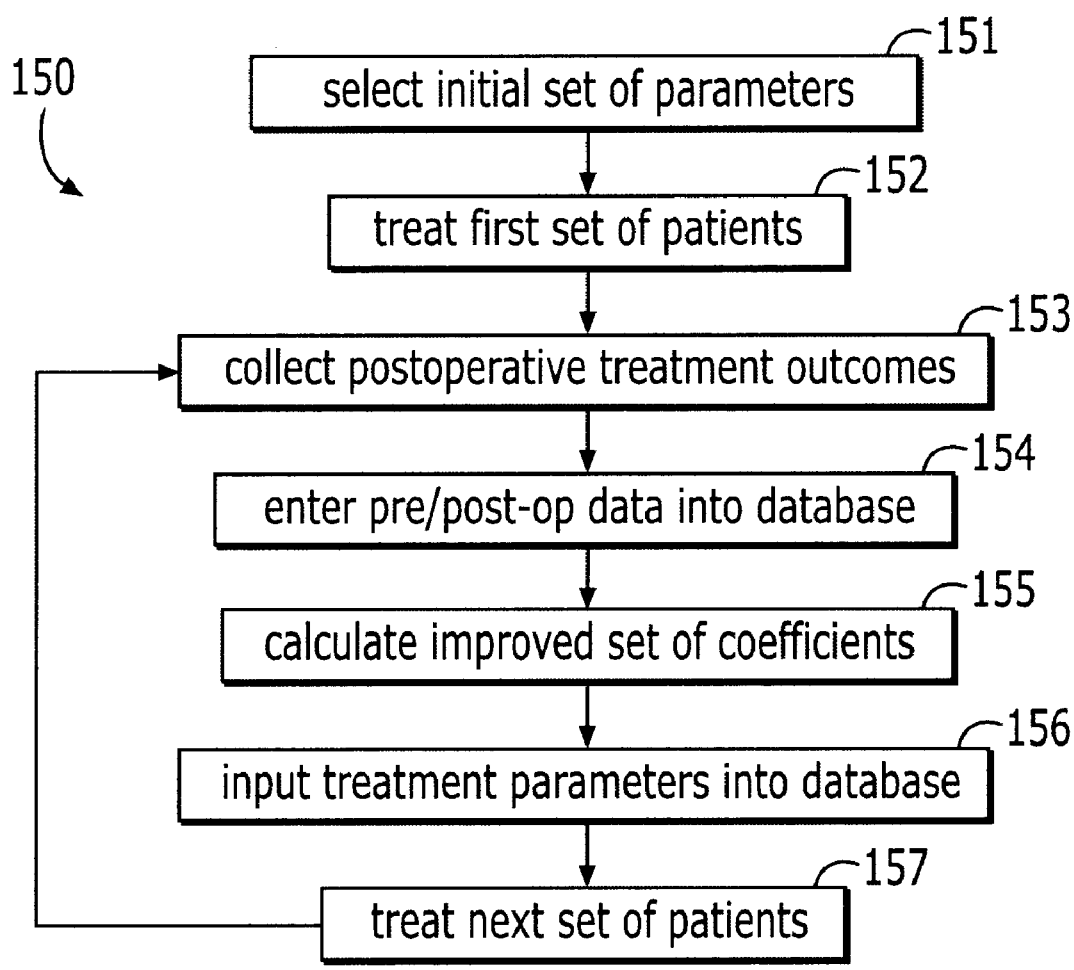
FIG. 4 is a flow chart of a method for creating a database of treatment outcomes.

A database 14 of treatment outcomes on a plurality of previously treated patients, which is created in steps such as illustrated in FIG. 4, is accessed (block 103) by the software package 13. Each treated patient outcome has associated therewith at least one classification element and comprises a preoperative wavefront-determined correction prescription and a postoperative visual profile.

From the treatment outcomes in the database 14 is calculated an average difference between the preoperative prescription and the postoperative profile for at least some of the previously treated patients having a classification element in common with the current patient (block 104). As preferred embodiments only, three methods for achieving an optimized prescription from this calculation step will be presented herein (block 105). In the first method 100, illustrated in FIGS. 2A and 2B, a linear scaling adjustment, the calculating step further comprises calculating from the average difference a percentage difference (block 106). The current patient correction prescription is then adjusted commensurate with the calculated average difference to form an optimized prescription, thereby avoiding a statistically calculable over- or undercorrection. In this embodiment 100, the adjusting step comprises multiplying the algorithm terms by the percentage difference (block 107), globally increasing or decreasing the wavefront profile, to form the optimized prescription (block 108).

Figure 2A:
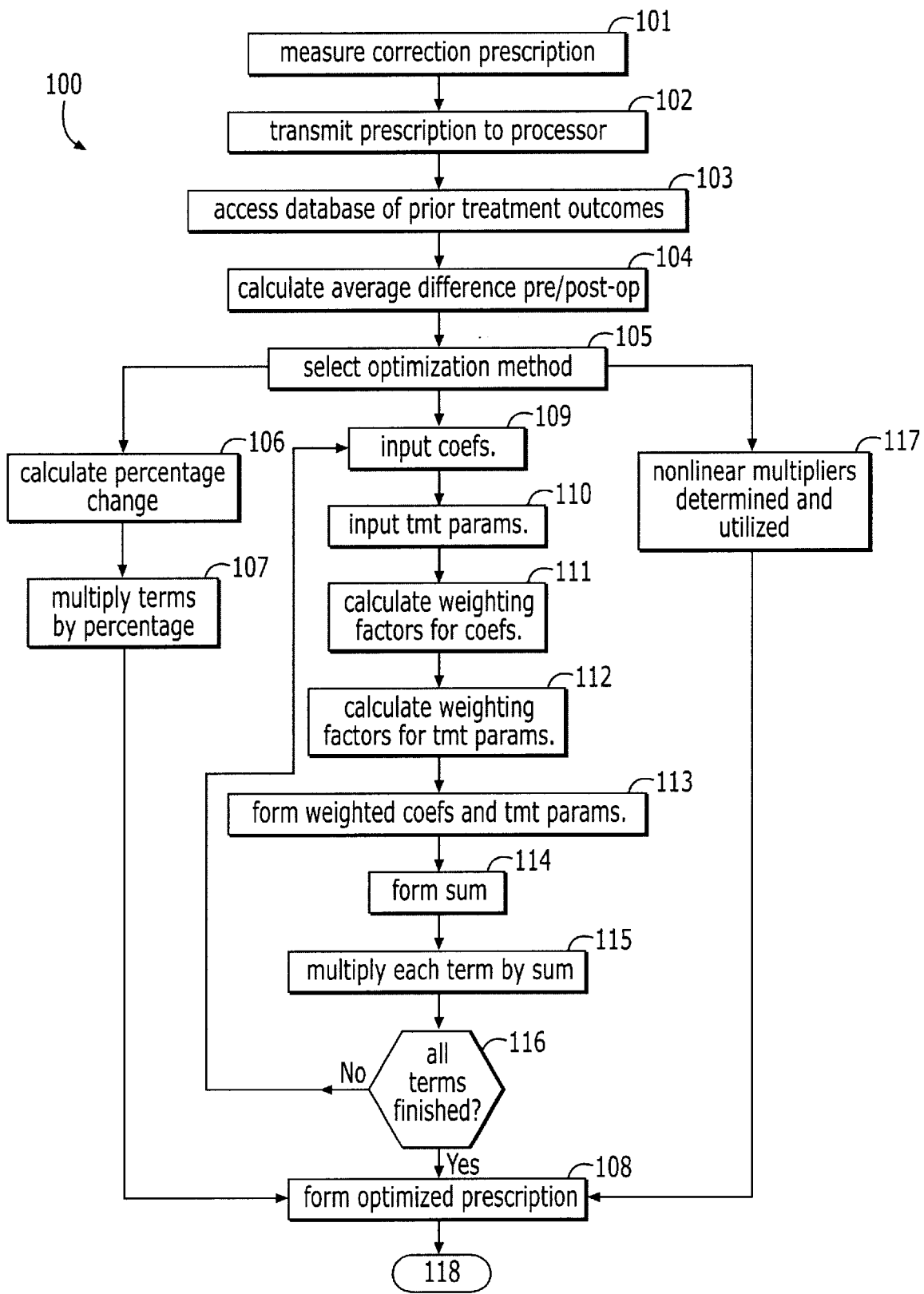
FIGS. 2A, 2B is a flow chart of a method for optimizing a treatment prescription for a current patient.
Figure 2B:
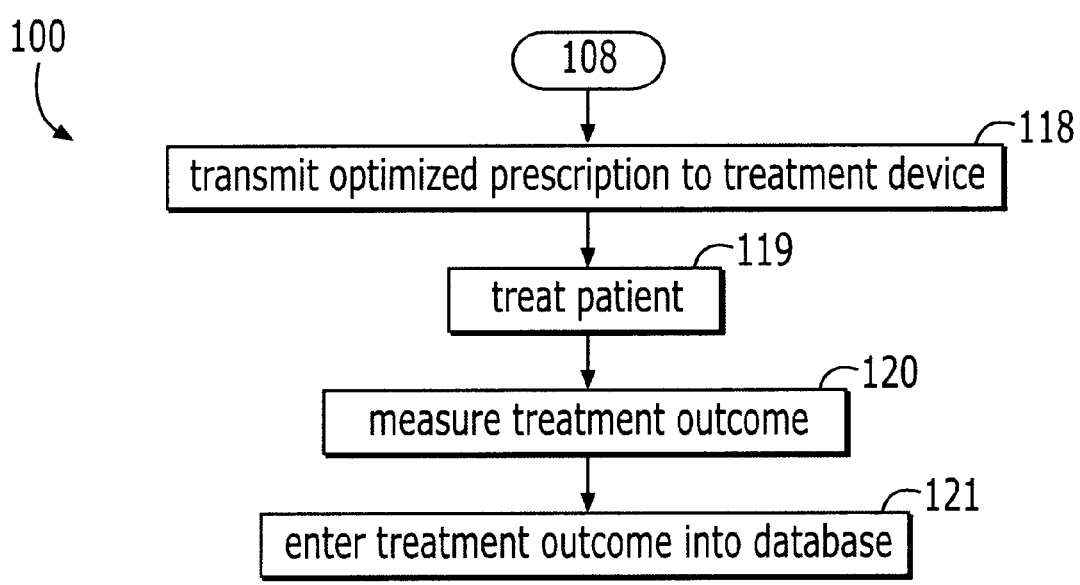
Figure 3:
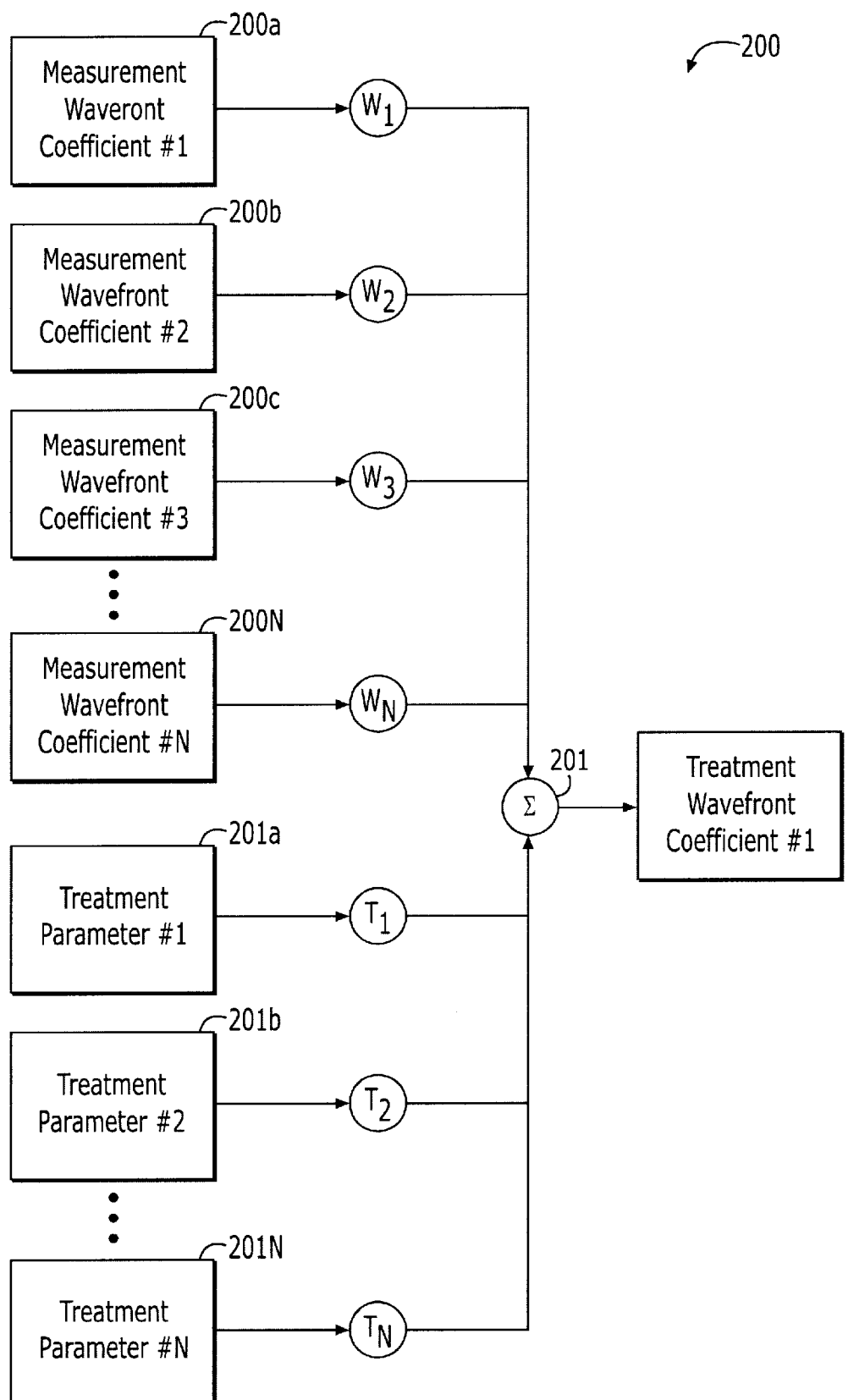
FIG. 3 illustrates an exemplary algorithm for calculating optimized coefficients for a treatment prescription.

In the second method 300, an algorithm for which is illustrated in FIG. 3, and the flow chart for which is shown in FIGS. 2A and 2B, a "nomogram"-type approach is used wherein an object of the optimization procedure is to arrive at a modified description of the measured wavefront, using the same mathematical notation scheme as used in determining the correction prescription. The goal of the modified description is to achieve an optimal treatment outcome when used to calculate the actual ablation treatment profile to be used on the patient.

In FIG. 3 is illustrated how the algorithm 200 of the present embodiment of the invention arrives at an optimized value for one output coefficient. In this aspect of the method 100, the data set input to the algorithm 200 includes the true coefficients of the measured wavefronts 200$a$, 200$b$, 200$c$, ..., 200N (block 109, FIG. 2A). Additional input data include input values for other treatment parameters 201$a$, 201$b$, ..., 201N (block 110). The treatment parameters may comprise such data as patient demographic parameter, such as age, gender, or ethnicity; a site-specific environmental parameter, such as site altitude, temperature, or humidity; and a flap parameter, such as expected flap thickness or hinge location.

In this algorithm 200, the calculating step then further comprises converting the calculated average difference into a weighting factor, shown in FIG. 3 as $W_1, W_2, W_3, \ldots, W_N$ for each of the coefficients associated with the wavefront determination algorithm terms (block 111), and also converting the calculated average difference into a weighting factor for the one treatment parameters, shown in FIG. 3 as $T_1, T_2, \ldots, T_N$ (block 112). The adjusting step comprises multiplying each coefficient and treatment parameter by the respective weighting factor to form weighted coefficients and weighted treatment parameters (block 113). Next the weighted coefficients for each term and the weighted treatment parameters are summed (block 114; "Σ" 201 in FIG. 3), and each term is multiplied by the sum of the weighted coefficients and weighted treatment parameters (block 115).

This procedure (blocks 109-115) is continued for all terms in the wavefront description (block 116) until a complete optimized prescription is formed (block 108).

It will be understood by one of skill in the art that this particular embodiment represents an exemplary method, and that alternate embodiments may be envisioned without departing from the spirit of the invention. For example, in a third embodiment (FIG. 2A), a nonlinear approach may be utilized wherein at least some the weighting coefficients are not simple linear multipliers (block 117), such as coefficients that change depending upon the input value, or are influenced by other factors in an interdependent manner. As this system 10 and method embodiments 100 are conceived to be adaptive, it will be appreciated by one of skill in the art that an algorithm that "learns" from new input data is possible when the database has sufficient data therein from which to form statistically valid correlations.

Once an optimized prescription is determined (block 108) from any of the methods, the optimized prescription may be automatically transmitted to a treatment device 15 (block 118, FIG. 2B). Alternatively, the calculations may be made within the processor 12 following transmission of the raw prescription data to the treatment device 15.

Preferably, following each treatment (block 119) of a current patient, a treatment outcome on the current patient is measured (block 120) at a predetermined interval following the treatment. In order to continuously enrich the database, the treatment outcome for the current patient is then entered into the database (block 121).

Another embodiment of the present invention includes a method 150 for the creation of a system from which to extract optimization data for use in the previously described method 100. In this aspect of the invention, a flowchart for which is given in FIG. 4, an initial set of parameters are selected (block 151), with the weighting coefficients set to nominal values. For example, the weights may be set to translate the measurement wavefront directly into the treatment wavefront without modification. In FIGS. 2A and 2B, this would correspond to $W_1$ 220$a$ being equal to 1 and all other terms being equal to 0 for determining the first treatment wavefront coefficient.

Using this initial set of parameters, a first set of patients are treated (block 152), and postoperative treatment outcomes are collected after a predetermined interval (block 153). The pre- and postoperative data, along with the associated classification element(s), are entered into a database 14 (block 154).

A search engine 16 resident on the processor 12 is adapted to extract treatment outcomes based upon a classification element desired for correlation calculations. As above, an improved set of coefficients can then be calculated (block 155) for a second set of patients using these data.

Treatment outcomes from the second set of patients are then entered into the database 14 (block 156), thereby further improving the statistics for the data. This process can be continued with a next set of patients (block 157), and further continued essentially indefinitely, shown by the return arrow to block 153 in FIG. 4, to further refine the adjustment algorithm.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details disclosed herein.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for optimizing a prescription for laser-ablation corneal treatment comprising the steps of:

receiving a measured correction prescription for a current patient having a classification element associated therewith, the correction prescription having been measured using a wavefront determination;

accessing a database of treatment outcomes on a plurality of previously treated patients, each treated patient outcome having associated therewith at least one classification element and comprising a preoperative wavefront-determined correction prescription and a postoperative visual profile;

calculating from the treatment outcomes in the database an average difference between the preoperative prescription and the postoperative profile for at least some of the previously treated patients having a classification element in common with the current patient; and adjusting the current patient correction prescription commensurate with the calculated average difference to form an optimized prescription.

2. The method recited in claim 1, wherein:

the correction prescription comprises an algorithm having a plurality of terms;

the calculating step further comprises calculating from the average difference a percentage difference; and the adjusting step comprises multiplying the algorithm terms by the percentage difference.

3. The method recited in claim 1, wherein the adjusting step comprises automatically transmitting the optimized prescription to a treatment device.

4. The method recited in claim 1, wherein:

the correction prescription comprises a raw prescription; and the adjusting step comprises automatically adjusting the raw prescription to form the optimized prescription.

5. The method recited in claim 1, further comprising the steps of:

measuring a treatment outcome on the current patient at a predetermined interval following laser-ablation corneal treatment; and entering the treatment outcome for the current patient into the database.

6. The method recited in claim 1, wherein:

the wavefront determination comprises an algorithm comprising a plurality of terms, each term having associated therewith a coefficient;

the calculating step further comprises converting the calculated average difference into a weighting factor for each coefficient; and the adjusting step comprises multiplying each coefficient by the respective weighting factor to form a weighted coefficient, summing the weighted coefficients for each term, and multiplying each term by the sum of the weighted coefficients to form the optimized prescription.

7. The method recited in claim 6, wherein:

the calculating step further comprises converting the calculated average difference into a weighting factor for at least one treatment parameter resident in the database;

the adjusting step further comprises multiplying each treatment parameter by the respective weighting factor to form a weighted treatment parameter, the summing step further includes adding the weighted treatment parameter to the summed weighted coefficients for each term, and the term-multiplying step comprises multiplying each term by the sum of the weighted coefficients and weighted treatment parameter to form the optimized prescription.

8. The method recited in claim 7, wherein the treatment parameter comprises at least one of a patient demographic parameter, a site-specific environmental parameter, and a flap parameter.

9. The method recited in claim 1, wherein:

the wavefront determination comprises an algorithm comprising a plurality of terms, each term having associated therewith a coefficient;

the calculating step further comprises converting the calculated average difference into a weighting factor for each coefficient;

the adjusting step comprises determining and performing an optimal application of the respective weighting factor to each coefficient to form a weighted coefficient, summing the weighted coefficients for each term, and multiplying each term by the sum of the weighted coefficients to form the optimized prescription.

10. A method for creating a system for an optimizing a prescription for laser-ablation corneal treatment comprising the steps of:

forming a database of treatment outcomes on a plurality of treated patients, each treated patient outcome having associated therewith at least one classification element and comprising a preoperative wavefront-determined correction prescription and a postoperative visual profile;

providing a search engine resident on a processor adapted to extract treatment outcomes based upon a classification element;

providing software means resident on the processor adapted to calculate from the extracted treatment outcomes in the database an average difference between the preoperative prescription and the postoperative profile for at least some of the previously treated patients having a classification element in common with the current patient; and providing software means resident on the processor adapted to adjust a current patient correction prescription commensurate with the calculated average difference to form an optimized prescription, the current patient having a classification element associated therewith and having had a wavefront determination made for measuring an initial correction prescription.

11. The method recited in claim 10, further comprising the steps of:

measuring a treatment outcome on the current patient at a predetermined interval following treatment; and entering the treatment outcome for the current patient into the database.

12. A system for optimizing a prescription for laser-ablation corneal treatment comprising:

a wavefront measurement apparatus for determining a correction prescription for a current patient, the current patient having a classification element associated therewith;

a processor having software means resident thereon for:
accessing a database of treatment outcomes on a plurality of previously treated patients, each treated patient outcome having associated therewith at least one classification element and comprising a preoperative wavefront-determined correction prescription and a postoperative visual profile;

calculating from the treatment outcomes in the database an average difference between the preoperative prescription and the postoperative profile for at least some of the previously treated patients having a classification element in common with the current patient; and adjusting the current patient correction prescription commensurate with the calculated average difference to form an optimized prescription.

13. The system recited in claim 12, wherein:
the correction prescription comprises an algorithm having a plurality of terms;
the calculating means further comprises means for calculating from the average difference a percentage difference; and
the adjusting means comprises means for multiplying the algorithm terms by the percentage difference.

14. The system recited in claim 12, wherein the adjusting means comprises means for automatically transmitting the optimized prescription to a treatment device.

15. The system recited in claim 12, wherein:
the correction prescription comprises a raw prescription; and
the adjusting means comprises means for automatically correcting the raw prescription to form the optimized prescription.

16. The system recited in claim 12, wherein the software means further comprises means for entering a measured treatment outcome for the current patient into the database, the measured treatment outcome determined at a predetermined interval following treatment.

17. The system recited in claim 12, wherein:
the correction prescription comprises an algorithm comprising a plurality of terms, each term having associated therewith a coefficient;
the calculating means further comprises means for converting the calculated average difference into a weighting factor for each coefficient; and
the adjusting means comprises means for multiplying each coefficient by the respective weighting factor to form a weighted coefficient, means for summing the weighted coefficients for each term, and means for multiplying each term by the sum of the weighted coefficients to form the optimized prescription.

18. The system recited in claim 17, wherein:
the calculating means further comprises means for converting the calculated average difference into a weighting factor for at least one treatment parameter resident in the database;
the adjusting means further comprises means for multiplying each treatment parameter by the respective weighting factor to form a weighted treatment parameter, the summing means further includes means for adding the weighted treatment parameter to the summed weighted coefficients for each term, and the term-multiplying means comprises means for multiplying each term by the sum of the weighted coefficients and weighted treatment parameter to form the optimized prescription.

19. The system recited in claim 18, wherein the treatment parameter comprises at least one of a patient demographic parameter, a site-specific environmental parameter, and a flap parameter.

20. The system recited in claim 12, wherein:
the wavefront determination comprises an algorithm comprising a plurality of terms, each term having associated therewith a coefficient;
the calculating step further comprises converting the calculated average difference into a weighting factor for each coefficient;
the adjusting step comprises determining and performing an optimal application of the respective weighting factor to each coefficient to form a weighted coefficient, summing the weighted coefficients for each term, and multiplying each term by the sum of the weighted coefficients to form an optimized prescription.

21. A software package for optimizing a prescription for laser-ablation corneal treatment comprising means for:
receiving a correction prescription for a current patient, the current patient having a classification element associated therewith;
accessing a database of treatment outcomes on a plurality of previously treated patients, each treated patient outcome having associated therewith at least one classification element and comprising a preoperative wavefront-determined correction prescription and a postoperative visual profile;
calculating from the treatment outcomes in the database an average difference between the preoperative prescription and the postoperative profile for at least some of the previously treated patients having a classification element in common with the current patient; and
adjusting the current patient correction prescription commensurate with the calculated average difference to form an optimized prescription.

22. A method for optimizing a laser refractive surgical procedure comprising the steps of:
measuring a required corrective prescription for a current patient using a wavefront-based diagnostic device;
assigning a classification number to the current patient, the classification number being based at least in part on the measured corrective prescription;
comparing the measured corrective prescription of the current patient with a plurality of prior patients having a similar classification number, such prior patients having a wavefront-measured predicted preoperative refractive correction and a wavefront-measured achieved postoperative refractive correction; and
adjusting the measured corrective prescription for the current patient based on a difference between the wavefront-measured predicted preoperative refractive correction and the wavefront-measured achieved postoperative refractive correction of the plurality of prior patients.

* * * * *